(12) United States Patent
Bodenweber et al.

(10) Patent No.: US 9,366,591 B2
(45) Date of Patent: Jun. 14, 2016

(54) DETERMINING MAGNITUDE OF COMPRESSIVE LOADING

(71) Applicant: International Business Machines Corporation, Armonk, NY (US)

(72) Inventors: Paul F. Bodenweber, Kingston, NY (US); Virendra R. Jadhav, Redmond, WA (US); Steven P. Ostrander, Poughkeepsie, NY (US); Kamal K. Sikka, Poughkeepsie, NY (US); Jiantao Zheng, Beacon, NY (US); Jeffrey A. Zitz, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 77 days.

(21) Appl. No.: 14/339,944

(22) Filed: Jul. 24, 2014

(65) Prior Publication Data

US 2014/0331792 A1   Nov. 13, 2014

Related U.S. Application Data

(62) Division of application No. 13/289,121, filed on Nov. 4, 2011, now Pat. No. 8,794,079.

(51) Int. Cl.
*G01N 3/08* (2006.01)
*G01L 5/00* (2006.01)
*G01N 27/22* (2006.01)

(52) U.S. Cl.
CPC .............. *G01L 5/0038* (2013.01); *G01L 5/0057* (2013.01); *G01L 5/0076* (2013.01); *G01N 3/08* (2013.01); *G01N 27/22* (2013.01); *G01N 2203/0617* (2013.01); *G01N 2203/0629* (2013.01); *G01N 2203/0682* (2013.01)

(58) Field of Classification Search
CPC .......... G01L 5/0057; G01L 27/22; G01L 3/00
USPC ..................................................... 73/760, 818
See application file for complete search history.

(56) References Cited

U.S. PATENT DOCUMENTS 3,774,440 A * 11/1973 Martinelli .............. G01N 25/04
                                                      374/52
5,171,403 A   12/1992 Chase et al.
(Continued)

FOREIGN PATENT DOCUMENTS

JP          2002257655 A        9/2002

OTHER PUBLICATIONS

Non-Final Office Action issued in U.S. Appl. No. 13/289,121 on Dec. 27, 2013; 11 pages.

*Primary Examiner* — Max Noori
(74) *Attorney, Agent, or Firm* — Cantor Colburn LLP; Steven Meyers

(57) ABSTRACT

An apparatus for determining a magnitude of a compressive load applied to a piston including a compliant film disposed between first and second elements is provided. The apparatus includes a first part movable with the first element in a movement direction along which the magnitude of the compressive load is to be determined, a second part movable with the second element in the movement direction and a sensor to measure a distance between the first and second parts in the movement direction, the measured distance being related to a deformation of the compliant film as the compressive load is applied.

12 Claims, 3 Drawing Sheets

(56) References Cited

U.S. PATENT DOCUMENTS

| | | | |
|---|---|---|---|
| 5,187,987 A * | 2/1993 | Anderson | G01N 3/20 73/852 |
| 5,305,634 A | 4/1994 | Suga et al. | |
| 5,437,192 A | 8/1995 | Kawamoto et al. | |
| 5,697,381 A | 12/1997 | Rantala et al. | |
| 6,457,624 B1 * | 10/2002 | Weihrauch | B25C 1/14 173/211 |
| 6,606,914 B2 | 8/2003 | Kume | |
| 7,214,200 B2 | 5/2007 | Raney et al. | |
| 7,395,721 B2 | 7/2008 | Taniguchi | |
| 7,459,626 B2 | 12/2008 | Yoshino et al. | |
| 7,475,606 B2 | 1/2009 | Selig et al. | |
| 7,570,065 B2 | 8/2009 | Harish et al. | |
| 7,654,159 B2 | 2/2010 | Enoksson et al. | |
| 8,461,860 B2 | 6/2013 | Kim et al. | |
| 8,544,340 B1 | 10/2013 | Ardelean et al. | |
| 8,551,025 B2 | 10/2013 | Soltz | |
| 2007/0069354 A1 * | 3/2007 | Dangelmaier | B81B 7/0058 257/678 |
| 2009/0178493 A1 | 7/2009 | Stratmann et al. | |
| 2009/0259412 A1 * | 10/2009 | Brogardh | B25J 9/1633 702/41 |
| 2011/0023631 A1 | 2/2011 | Sleeman | |
| 2011/0067565 A1 * | 3/2011 | Steinich | F15B 1/24 92/5 R |

\* cited by examiner

DETERMINING MAGNITUDE OF COMPRESSIVE LOADING

This application is a divisional application that claims the benefit of priority to U.S. application Ser. No. 13/289,121, which was filed on Nov. 4, 2011 and is now allowed. The entire contents of U.S. application Ser. No. 13/289,121 are incorporated herein by reference.

BACKGROUND

The present invention relates generally to semiconductor device manufacturing and, more specifically, to an apparatus and method for determining a load between a processor and a heat spreader An electronic package typically includes a substrate, a processor, an array of electrical connections between the substrate and the processor, a thermal interface material (TIM) and a heat spreader. During operation of the chip, the heat generated by the processor is transferred from the processor, through the TIM and into the heat spreader so that a temperature of the processor can be maintained at or below a predetermined level.

During late assembly processes of electronic packages, the electronic packages are often placed under compressive loads, which generate high compression forces on various components of the electronic packages. These compression forces can lead to electrical failures of the processor if a magnitude of the compression forces exceeds certain levels. It is, therefore, often necessary to measure and monitor the compressive load between the heat spreader and the processor. Such measurement and monitoring is difficult, however, due to the effectively limited compliance in the TIM in the late assembly stages and the limited space available to accommodate traditional load cells.

SUMMARY

According to an aspect of the present invention, an apparatus for determining a magnitude of a compressive load is provided. The apparatus includes a first part movable with a first element in a movement direction along which the magnitude of the compressive load is to be determined, a second part movable with a second element in the movement direction and a sensor to measure a distance between the first and second parts in the movement direction, the measured distance being related to a deformation of a compliant film disposed between the first and second elements as the compressive load is applied.

According to another aspect of the present invention, an apparatus for determining a magnitude of a compressive load is provided. The apparatus includes a cap affixed to and movable with an upper portion of a piston in a movement direction along which the magnitude of the compressive load is to be determined, a spring disposed in contact with the cap, a pin disposed to extend through the upper portion of the piston and urged by the spring toward a lower portion of the piston, the pin being thereby movable with the lower portion of the piston in the movement direction and a sensor to measure a distance between the cap and the pin in the movement direction, the measured distance being related to a deformation of a compliant film disposed between the upper and lower portions as the compressive load is applied.

According to another aspect of the invention, a method for determining a magnitude of a compressive load is provided. The method includes machining a through-hole in an upper portion of a piston, disposing in the through-hole a sensor assembly apparatus including a cap movable with the upper portion of the piston and a pin movable with a lower portion of the piston and operating the sensor assembly apparatus to measure a distance between the cap and the pin, the measured distance being related to a deformation of a compliant film disposed between the upper and lower portions as the compressive load is applied.

According to yet another aspect of the invention, an apparatus to measure a magnitude of force applied to a device packaged between a substrate and a lid is provided. The apparatus includes an elastic element embedded within the lid, which is deformatively responsive to the applied force and a sensor embedded within the lid to measure deformation of the elastic element, the magnitude of the applied force being derivable from the measured deformation.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
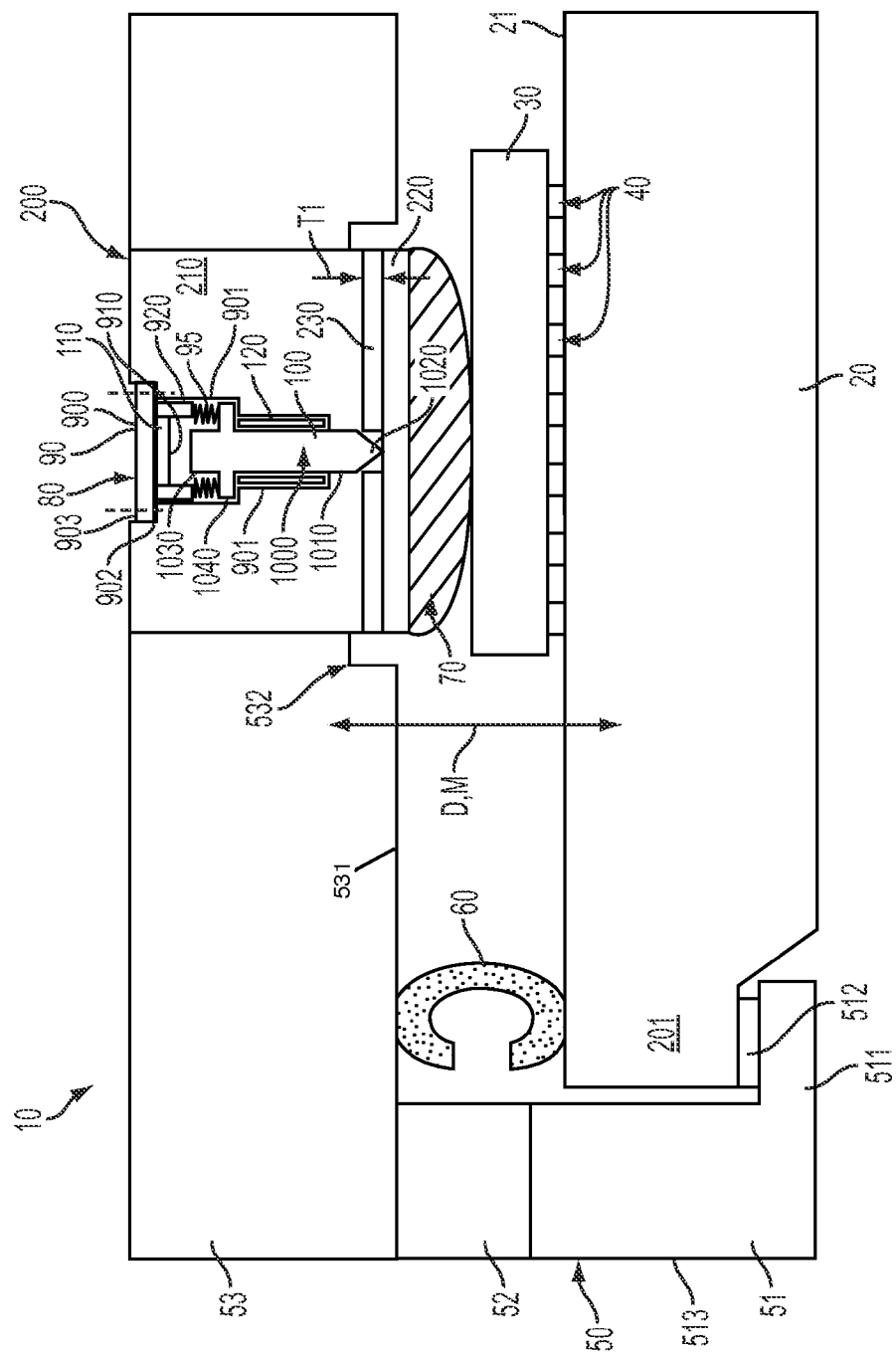
FIG. 1 is a schematic side view of an electronic package.

With reference now to FIG. 1, an electronic package 10 is provided. The electronic package includes a substrate 20 and a chip, integrated circuit (IC) or processor 30. The substrate 20 has a top surface 21 on which electronic leads are arrayed. The processor 30 is disposed above the top surface 21 and electrically communicates with the electronic leads via soldered electrical connections 40. The substrate 20 is disposed within a lid structure 50, which includes a base plate 51, shims 52 and a lid 53, which is made of metallic thermally conductive materials, such as copper. The base plate 51 includes a plate section 511 having an edge on which a cushion 512 is provided and a wall section 513, which is vertically extended from the plate section 511. An outer rim portion 201 of the substrate overlaps with and sits upon the cushion 512. The shims 52 support the lid 53 such that a lower surface 531 of the lid 53 opposes the top surface 21 of the substrate 20 and the processor 30. The shims 52 sit upon an upper edge of the wall section 513 whereby the shims 52 permit vertical movement of the lid 53. The electronic package 10 further includes a compliant part 60, such as a c-ring, that is disposed between the lower surface 531 of the lid 53 and the top surface 21 of the substrate 20 to provide a bias against downward vertical movement of the lid 53 toward the substrate 20 as well as a seal.

The lid 53 is formed to define a through-hole in which a piston 200 is receivable. The piston 200 may be substantially cylindrical and the through-hole may be annular in shape. Sidewalls of the piston 200 are connected to inwardly facing sidewalls of the through-hole by solder. In this way, during initial processing operations, the piston 200 can be vertically displaced toward the processor 30 by heating the solder and allowing the piston 200 to displace in a gravitation field toward the processor 30. The displacement is ultimately prevented by a dummy layer of a given thickness (i.e., 30 μm), which is removed and replaced by a thermal interface layer to be described below.

The piston 200 includes an upper portion 210, a lower portion 220 and a thin compliant film 230, which is interposed between the upper portion 210 and the lower portion 220. At the lower surface 531 of the lid 53, the lid 53 is further formed to define a recess 532 about the through-hole at a lower section of the upper portion 210, the thin compliant film 230 and the lower portion 220. With this construction, the piston 200 is able to respond elastically to compressive forces acting through its longitudinal axis (i.e., through the piston 200 from the upper portion 210 to the lower portion 220).

Thermal interface material (TIM) 70 is provided between the lower portion 220 of the piston 200 and the processor 30. During operation of the electronic package 10, the processor 30 generates heat that is transmitted to the lid 53, which acts as a heat spreader, via the TIM 70 and, in this way, a temperature of the processor 30 can be maintained at or below a predetermined safe operational level. During assembly processes of the electronic package 10, compressive loads are applied to the lid 53 and the piston 200. In early assembly processes, the compressive loads serve to place the lower portion 220 at a certain distance from the processor 30, as described above, such that the TIM 70 can be interposed between the lower portion 220 and the processor 30 with a predefined thickness (i.e., approximately 30 μm). In later processes, the compressive loads serve to facilitate electrical connectivity between a printed circuit board and the substrate 20 via a $2^{nd}$ level connector, such as a land grid array. It has been observed, however, that if a magnitude of the compressive loads exceeds certain safe or predefined levels, part of the compressive loads will be transferred to the processor 30, and the soldered electrical connections 40 can generate filaments that can lead to electrical shorts and/or other failures.

Thus, it is to be understood that a magnitude of the compressive loading of the piston 200 in a substantially vertical direction, D, can be a significant factor in the proper function of the electronic package 10 following assembly. In particular, a magnitude of the compressive loading should be maintained below magnitudes at which electrical failures are made more likely without being reduced to the point where the soldered electrical connections 40 fail to become established. With this in mind, aspects of the present invention provide for in situ measurement and monitoring of a magnitude of the compressive loading of the piston 200 using, for example, capacitive sensors during module assembly and in field applications.

In accordance with aspects of the invention, a sensor assembly apparatus 80 for determining a magnitude of the compressive loading of the piston 200 is provided. The sensor assembly apparatus 80 includes a first part 90, which is movable with the lid 53 and the upper portion 210 of the piston 200 (i.e., a first element) in a movement direction, M. The movement direction, M, may be aligned with the substantially vertical direction, D, and defines a dimension along which a magnitude of the compressive loading is to be measured and monitored. The sensor assembly apparatus 80 also includes an elastic element 95, a second part 100, which is movable with the lower portion 220 of the piston 200 in the movement direction, M, a sensor 110 and a bushing 120.

The first part 90 may be formed as a cap 900 that is set into a through-hole 901 formed in the upper portion 210 of the piston 200 by, for example, machining. The through-hole 901 may include shoulder portions 902 on which cap edges 903 sit. The cap edges 903 may be affixed to the shoulder portions 902 by, for example, solder or welding (see dotted lines). The shoulder portions 902 and a thickness of the cap 900 are designed such that, when the cap 900 is installed with the cap edges 903 affixed to the shoulder portions 902, a plane of a top surface of the cap 900 is recessed from a plane of the top surface of the lid 53 and the top surface of the upper portion 210 of the piston 200. In this way, compressive loading can be applied to the lid 53 and the piston 200 but not the cap 900.

The cap 900 includes a plate 910, which may be formed of metallic and/or electrically conductive materials, and sidewalls 920 that extend downwardly. The elastic element 95 is disposed in contact with the lower edge of the sidewalls 920 and may be anchored thereto. The elastic element 95 may be a spring, such as a compression spring, or any other compliant element. In any case, the elastic element 95 is operably interposed between the first part 90 and the second part 100 and is thereby configured to urge the second part 100 to contact the lower portion 220 of the piston 200 (i.e., a second element).

The second part 100 includes a pin 1000, made from, for example, copper, which is oriented to extend substantially in the movement direction, M. The pin 1000 includes a body 1010, a tip 1020 at an end of the body 1010 that contacts an upper surface of the lower portion 220 of the piston 200, a sensor part 1030 provided at the other end of the body 1010 and a flange 1040. The sensor part 1030 may be formed of metallic and/or electrically conductive materials similar to those of the plate 910. The flange 1040 extends radially outwardly from the body 1010. The elastic element 95 applies a bias thereof to the flange 1040.

The bushing 120 is disposed within the through-hole 901 about the pin 1000 and may be formed of, for example, plastic materials. The bushing 120 supports the orientation and movement of the pin 1000 is the movement direction, M, with limited friction.

Figure 2:
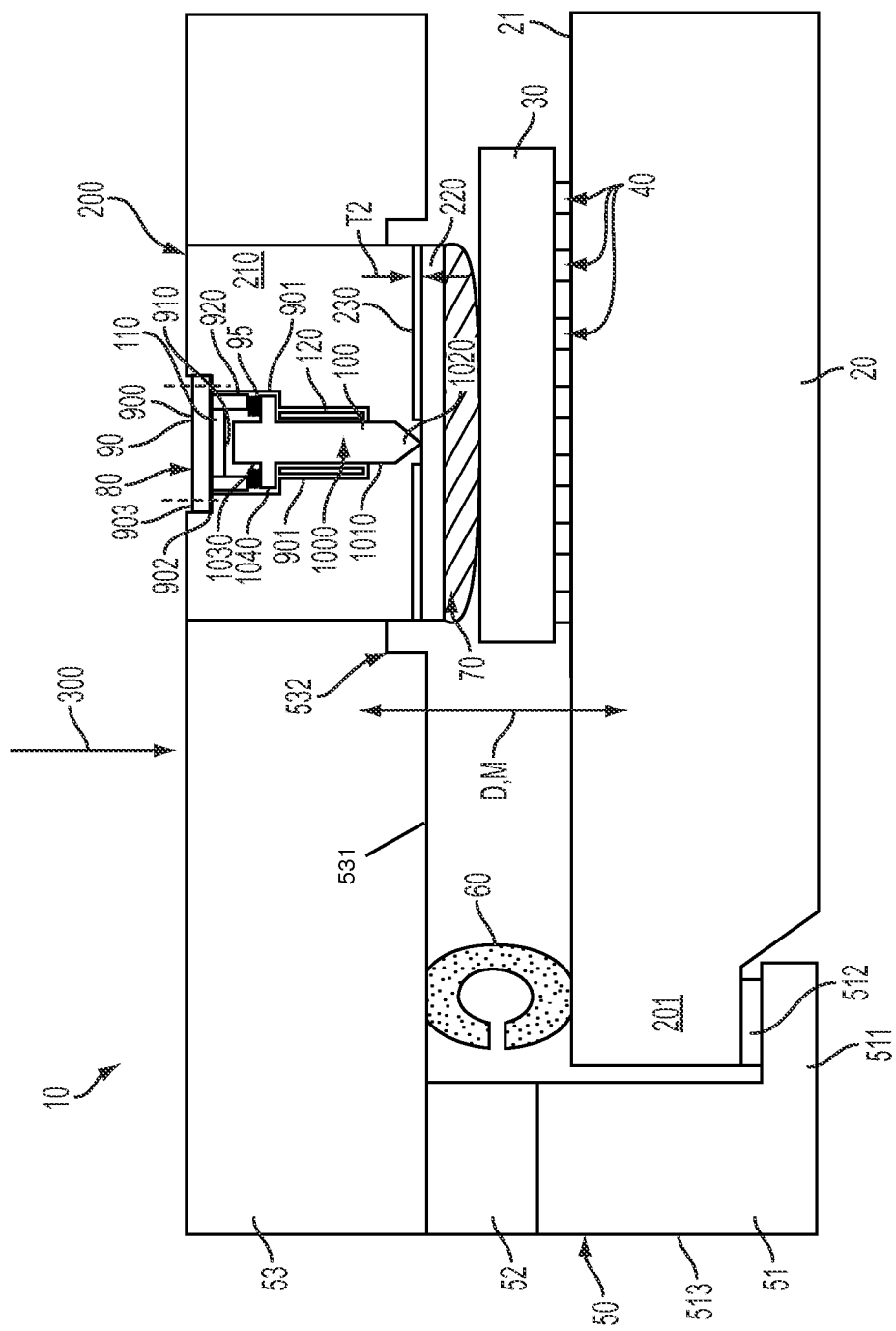
FIG. 2 is a schematic side view of the electronic package of FIG. 1 with a load applied thereto.

With reference to FIGS. 1 and 2, with the configuration described above, it is noted that the piston 200 is at least initially formed such that the thin compliant film 230 has a predefined first thickness, T1, as shown in FIG. 1 and a known characteristic compliance in response to compressive loading. At some time thereafter, however, a compressive load 300 may be applied to the lid 53 and the piston 200 but not the cap 900, as shown in FIG. 2. This compressive load 300 is substantially larger than the bias applied to the second part 100 by the elastic element 95 and, in fact, may be up to hundreds of pounds per square inch. The compressive load 300 therefore tends to compress the thin compliant film 230 toward a second thickness, T2.

That is, when the compressive load 300 is applied to the lid 53 and the piston 200, the thin compliant film 230 is compressed toward the second thickness, T2, and the cap 900 is forced downwardly in the movement direction, M, since the cap 900 is affixed to the upper portion 210 of the piston 200. The pin 1000 meanwhile remains in contact with the lower portion 220 of the piston 200. Thus, as the thin compliant film 230 is compressed, the plate 910 and the sensor part 1030 approach one another in the movement direction, M.

Figure 3:
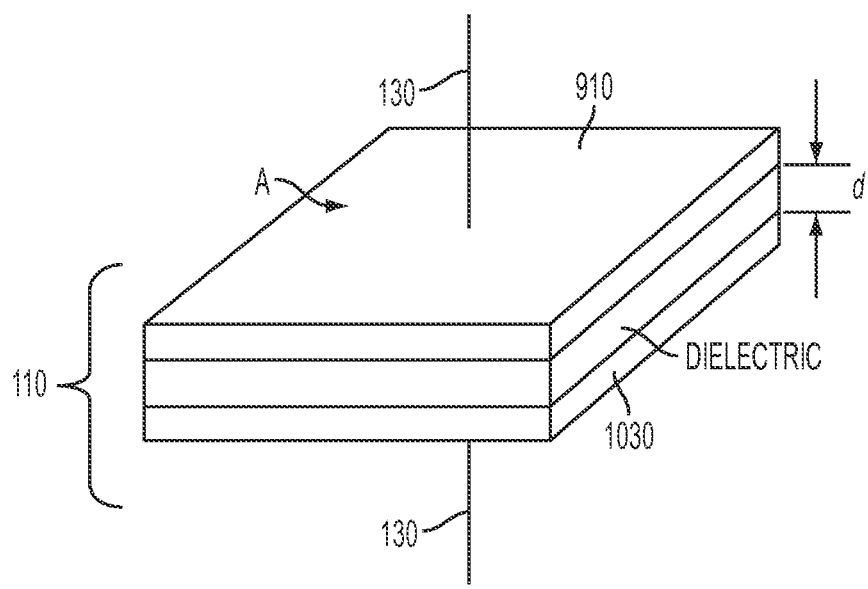
FIG. 3 is a perspective view of a sensor of the electronic package of the FIG. 1.

With reference to FIG. 3 and, in accordance with an embodiment of the invention, the sensor 110 may be a capacitive sensor that includes the plate 910 and the sensor part 1030 as well as leads 130. As shown in FIG. 3, the plate 910 and the sensor part 1030 are each plate-like in appearance and arranged in parallel with one another with a dielectric material interposed between them. As an example, the dielectric material may be air or vacuum space. In either case, a capacitance, C, measured by the sensor 110 is equal to $\in_r *\in_0 *A/d$), where $\in_r$ is the relative static permittivity (or dielectric constant) of the material between the plate 910 and the sensor part 1030, $\in_0$ is the electric constant, A is the area of overlap of the plate 910 and the sensor part 1030 and is the separation between the plate 910 and the sensor part 1030 in the movement direction, M.

Thus, it can be seen that the sensor 110 will record an increased capacitance as the compressive load 300 is applied and the thin compliant film 230 is deformed such that its thickness decreases. The sensor 110 is thus configured to measure a distance between the first and second parts 90 and 100 in the movement direction, M. In most cases, the measured distance is directly related to the compliance film 230 thickness, such that the measured distance provided by the sensor 110 provides a direct indication of the thin compliant film 230 thickness. Since compliance characteristics of the thin compliant film 230 may be known, the deformation of the thin compliant film 230 can be used to determine a magnitude of the compressive load 300.

Often, the relationship between the measured distance and the thin compliant film 230 thickness will be substantially a 1:1 relationship. Where this is not the case due to, for example, part deformation, the non 1:1 relationship may still be known and accounted for by the sensor 110 and/or a computing device coupled to the sensor 110 via the leads 130.

Also, while the sensor 110 is described above as a capacitance sensor, it is understood that the sensor 110 can operate in accordance with multiple other sensing techniques. These include, but are not limited to, optical and/or electro-magnetic sensing techniques. Moreover, while the capacitance sensing described above provides a direct linear measurement of the distance between the cap 900 and the pin 1000, it is understood that other sensing techniques may be employed that would provide measurements that do not have a linear relationship with the distance. In these cases, the non-linear relationship would again be known and accounted for by the sensor 110 and/or a computing device coupled to the sensor 110 via the leads 130.

As described above, the sensor 110 senses the capacitance between the cap 900 and the pin 1000 through a given dielectric material (i.e., air or vacuum space). However, it is to be understood that the sensor 110 can be configured to sense the capacitance through multiple types of media and through media that changes during the loading operation.

In accordance with further aspects, a method for determining a magnitude of a compressive load 300 is provided and includes machining the through-hole 901 in the upper portion 210 of the piston 200 and disposing in the through-hole 901 a sensor assembly apparatus 80. As noted above, the sensor assembly apparatus includes a cap 900 to be movable with the lid 53 and the upper portion 210 of the piston 200 and a pin 1000 to be movable with the lower portion 220 of the piston 200. The method further includes operating the sensor assembly apparatus 80 to measure a distance between the cap 900 and the pin 1000 where the measured distance is related to the deformation of the thin compliant film 230 and therefore determinative of the magnitude of the compressive load 300. In accordance with the method, the disposing may include configuring the sensor assembly apparatus 80 with an elastic element 95, which is disposed in contact with the cap 900 and is configured to urge the pin 1000 toward the processor 30.

The method may further include compressively loading the lid 53 and the piston 200 to deform the thin compliant film 230. Here, the operating of the sensor assembly apparatus 80 may be conducted during the loading of the lid 53 and the piston 200 such that the deformation can be monitored and stopped when a predefined second thickness, T2, of the thin compliant film 230 is attained. As mentioned above, the operating of the sensor assembly apparatus 80 may include capacitance sensing between the cap 900 and the pin 1000. In addition, the method may include calculating the magnitude of the compressive load 300 from the deformation of the thin compliant film 230 and a known compliance of the thin compliant film 230. Once this calculation is complete, the method may further include limiting the magnitude of the compressive load 300 to remain below a predefined magnitude at which it is expected that electrical failures might not be avoided.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An apparatus for determining a magnitude of a compressive load, the apparatus comprising:
 a cap affixed to and movable with an upper portion of a piston in a movement direction along which the magnitude of the compressive load is to be determined;
 a spring disposed in contact with the cap;
 a pin disposed to extend through the upper portion of the piston and urged by the spring toward a lower portion of the piston, the pin being thereby movable with the lower portion of the piston in the movement direction; and
 a sensor to measure a distance between the cap and the pin in the movement direction, the measured distance being related to a deformation of a compliant film disposed between the upper and lower portions as the compressive load is applied.

2. The apparatus according to claim 1, wherein a plane of a surface of the cap is recessed from a corresponding plane of a surface of the upper portion of the piston.

3. The apparatus according to claim 1, further comprising a bushing disposed within the upper portion of the piston through which the pin extends.

4. The apparatus according to claim 1, wherein the sensor comprises a capacitive sensor.

5. A method for determining a magnitude of a compressive load, the method comprising:
   machining a through-hole in an upper portion of a piston;
   disposing in the through-hole a sensor assembly apparatus including a cap movable with the upper portion of the piston and a pin movable with a lower portion of the piston; and
   operating the sensor assembly apparatus to measure a distance between the cap and the pin, the measured distance being related to a deformation of a compliant film disposed between the upper and lower portions as the compressive load is applied.

6. The method according to claim 5, wherein the disposing comprises configuring the sensor assembly apparatus with an elastic element, which is disposed in contact with the cap and configured to urge the pin toward the lower portion of the piston.

7. The method according to claim 5, further comprising loading the upper portion of the piston to deform the compliant film.

8. The method according to claim 5, wherein the operating of the sensor assembly apparatus is conducted during the loading of the upper portion of the piston.

9. The method according to claim 5, wherein the operating of the sensor assembly apparatus comprises capacitance sensing between the cap and the pin.

10. The method according to claim 5, further comprising calculating the magnitude of the compressive load from the deformation of the compliant film and a known compliance of the compliant film.

11. The method according to claim 10, further comprising limiting the magnitude of the compressive load to remain below a predefined magnitude.

12. An apparatus for determining a magnitude of a compressive load, the apparatus comprising:
   a piston comprising an upper portion, a lower portion and a compliant film interposed between the upper and lower portions;
   a cap affixed to and movable with the upper portion in a movement direction along which the magnitude of the compressive load is to be determined;
   a spring disposed in contact with the cap;
   a pin comprising a body and a tip, the body being disposed to extend through the upper portion and an aperture defined by the thin compliant film such that the tip contacts an upper surface of the lower portion, the pin being urged by the spring toward the lower portion with the pin being thereby movable with the lower portion in the movement direction; and
   a sensor to measure a distance between the cap and the pin in the movement direction, the measured distance being related to deformation of the compliant film as the compressive load is applied.

* * * * *